US005540227A

United States Patent [19]

Poole

[11] Patent Number: 5,540,227
[45] Date of Patent: Jul. 30, 1996

[54] CONTROLLED APPLICATION OF SELECT OPHTHALMIC AGENTS

[76] Inventor: Thomas A. Poole, 333 E. 57th St., Apt. 12A, New York, N.Y. 10021

[21] Appl. No.: 443,071

[22] Filed: May 17, 1995

[51] Int. Cl.$^6$ ........................................................ A61B 3/16
[52] U.S. Cl. ............................ 128/652; 128/646; 128/651
[58] Field of Search ..................................... 128/645, 646, 128/647, 648, 649, 650, 651, 652

[56] References Cited

U.S. PATENT DOCUMENTS

| | | | |
|---|---|---|---|
| 4,735,209 | 4/1988 | Foody | 128/652 |
| 4,922,914 | 5/1990 | Segal et al. | 128/646 |
| 5,318,029 | 6/1994 | Palese . | |
| 5,343,861 | 9/1994 | Herman | 128/652 |

OTHER PUBLICATIONS

"Recommendations for Ophthalmic Practice in Relation to the Human Immunodeficiency Virus" pp. 1–6, vol. 5/Chap. 64 of Clinical Ophthalmology.
"APIC Guidelines for Infection Control Practice" pp. 99–117, vol. 18/No. 2, of the Apr. 1990, issue of American Journal Of Infection Control.
"Goldmann Tonometry and Fluorescein Solution: A Way to Avoid Contact Lens Staining" pp. 61–62, 324–327 of the Oct. 1991, issue of Clao Journal.
"The ophthalmic rod: a new ophthalmic drug delivery system I" pp. 297–301 of the 1990, issue of Graefe's Archive Clinical And Experimental Ophthalmology.
"The ophthalmic rod: a new drug–delivery system II" pp. 302–304 of the 1990, issue of Graefe's Archive Clinical And Exerimental Ophthalmology.

*Primary Examiner*—Angela D. Sykes
*Assistant Examiner*—Stephen Huang
*Attorney, Agent, or Firm*—Hopgood, Caliamfde, Kalil & Judlowe

[57] ABSTRACT

An applicator device and procedure is disclosed directed to the controlled placement of a minute amount of fluorescein onto the cornea of a patient's eye. The fluorescein is used as a staining agent to permit applanation tonometric measurements. The fluorescein is applied with a disinfectant to the tonometer lens using a special applicator. The disinfectant evaporates leaving a thin film residue on the lens, which is subsequently redissolved in the tear film above the cornea.

The foregoing procedure enhances the tonometer measurements while simplifying the process and reducing risk of infective contaminates from entering the eye region.

6 Claims, 1 Drawing Sheet

CONTROLLED APPLICATION OF SELECT OPHTHALMIC AGENTS

FIELD OF THE INVENTION

The present invention relates to methods and apparatus for the controlled application of select OPHTHALMIC agents, and more particularly to the method of applying a fluorescein composition to permit specific ocular examinations, and the apparatus for enhanced application of the fluorescein composition during the examination using applanation tonometry.

BACKGROUND OF THE INVENTION

Ophthalmologists employ a wide variety of tools in examining eye conditions and assessing potential ocular damage and disease states. Testing and examination of the human eye is a particularly difficult process as the eye is a very fragile structure and is often sensitive to even the most benign compositions. Furthermore, the membranes around the eye and the ocular tissue are easily contaminated with infectious agents and provide a natural and effective growth media for these agents upon contact. This makes the design and implementation of examination procedures particularly difficult.

A well-known test commonly performed by ophthalmologists is referred to as applanation tonometry. This is a technique for assessing intra-ocular pressure with minimal intrusion to the patient. The evaluation of intra-ocular pressure is used to ascertain the existence of certain ocular problems such as glaucoma, that are evidenced by increased intraocular pressure. Applanation tonometry is practiced in a number of ways and is described in more detail in the following references—the contents of which are hereby incorporated by reference thereto as if restated here in full; see, specifically, "Recommendations for Ophthalmic Practice in Relation to the Human Immunodeficiency Virus" pages 1–6, Vol. 5/Chap. 64 of CLINICAL OPHTHALMOLOGY; "APIC Guidelines for Infection Control Practice" pages 99–117, Vol. 18/No. 2, of the April 1990, issue of AMERICAN JOURNAL OF INFECTION CONTROL; "Goldmann Tonometry and Fluorescein Solution: A Way to Avoid Contact Lens Staining" pages 61–62, 324–327 of the October, 1991, issue of CLAO JOURNAL; "The ophthalmic rod: a new ophthalmic drug delivery system I" pages 297–301 of the 1990, issue of GRAEFE'S ARCHIVE CLINICAL AND EXPERIMENTAL OPHTHALMOLOGY; "The ophthalmic rod: a new drug-delivery system II" pages 302–304 of the 1990, issue of GRAEFE'S ARCHIVE CLINICAL AND EXPERIMENTAL OPHTHALMOLOGY. The common procedure in applanation tonometry and tonometers in use requires the placement of a small amount of a staining agent, often fluorescein, onto the ocular tissue and contacting this tissue with a planar (applanations) lens surface to create a meniscus on the lens surface. As can be seen in FIG. 1, the capillary action of the fluid (25) between the lens (5) and the cornea tissue (15) forms a circular region the attributes of which in part are determined by the ocular pressure. These attributes include the angle that is formed by the meniscus and the contact area (35) of the lens to the cornea. By aligning the prism lens in the tonometer, the ophthalmologist gains information about ocular pressure.

As with most ocular examinations, there is significant concern about preventing infection to the ocular tissue when using the tonometer. The tonometer lens is made of a fragile polymer material that precludes the use of autoclaves or other heat based disinfecting processes or strong caustic solutions for disinfection, as these may craze or cloud the lens surface. Therefore, it is the common practice to apply a milder disinfectant onto the tip of the tonometer just prior to its use. The disinfectant that is typically used for this application is a seventy (70%) percent isopropyl alcohol, although ethyl alcohol also can be used. The disinfectant is applied by wiping the lens surface with a sponge containing the disinfectant. This procedure is considered sufficient to sterilize the tonometer from HIV and HBV viruses, but there remains some questions as whether this procedure is sufficient to sterilize the lens from adenovirus and other non-lipid (hydrophilic) viral agents.

In addition to the tonometer, the fluorescein solutions used in conjunction therewith must be provided in a sterile manner. Most ophthalmic solutions suppress bacterial growth with one or more preservatives—illustrative examples including benzalkonium chloride, chlorobutanol and chlorhexidine. However, fluorescein solutions are especially susceptible to bacterial infection. Because of this, a separate mechanism has been developed and is in use for its delivery. Fluorescein is stored on dry filter paper—just prior to dispensing the fluorescein, the filter paper is wetted with a sterile aqueous saline solution. Once placed in solution, the fluid is instilled into the conjunctival cul-de-sac, followed immediately by the initiation of the applanation procedure.

The foregoing procedures are difficult and time consuming to implement. Indeed, there have been many efforts to enhance sterile delivery of medicants to the eyes and significant research in this area. For example, in 1989, several papers were published on the use of an "ophthalmic rod" for the introduction of infection free medicants. See specifically, the articles [Insert references] the contents of which are herein incorporated by reference as if restated in full. This approach applies a dried medicant on the end of the thin rod which is then subjected to Gamma radiation—to insure complete destruction of any residual infectious agents. However, such a procedure has problems of its own and cannot be readily implemented for tonometry.

There has remained a need to enhance the examination procedure practiced by eye care specialist during the use of applanation tonometry. The present invention is directed to addressing this continuing need.

OBJECTS AND SUMMARY OF THE PRESENT INVENTION

It is an object of the present invention to provide a fluorescein delivery system during applanation tonometry procedures.

It is a further object of the present invention to provide a method for disinfection of a tonometer and applying a fluorescein solution for use during ophthalmic examination.

It is yet another object of the present invention to provide a system for delivering in a single step a solution for disinfection of a tonometer and a fluorescein composition for examination of ocular tissue.

The above and other objects of the present invention are realized in a novel applicator of fluorescein solution and a unique method for implementing the fluorescein solution introduction into the ocular tissue for use with the tonometer in assessing intraocular pressure. The applicator system includes a small absorbent pad, saturated with an antibacterial solvent—such as a 90 percent aqueous solution of isopropyl alcohol. This solvent further comprises the medicant (or indicator) at a preselected concentration. For a system delivering fluorescein, the concentration of fluorescein ranges between 0.01 to 1.0 percent as sodium fluorescein. The absorbent pad is stored in a sealed container until needed for a tonometry reading. At such time, the seal is broken and the fluorescein solution applied to the lens of the tonometer. The lens is thus disinfected by the alcohol solution—which quickly evaporates leaving a deposit of fluorescein evenly distributed over the tonometer lens surface. The applanation tonometer is then placed onto the ocular tissue where the tear film on the eye redissolves the fluorescein from the lens surface. The fluorescein is thus localized ideally beneath the tonometer lens and provides the requisite visible presentation to the examiner during the reading of the intraocular pressure.

In accordance with the varying aspects of the present invention, the application pad is stored in a cap receptacle corresponding in shape to the front portion of the tonometer to ease the application of the sterile solution thereto. The cap has a resealable film top that is removed from the forward end exposing the application solution. Use of a cap has the advantage of prolonged contact between the lens surface and disinfecting solution. An alternate arrangement provides a single use cap or pad.

The foregoing features of the present invention are more fully and readily understood from the following detailed description of a specific illustrative embodiment thereof, presented hereinbelow in conjunction with the accompanying drawings of which:

DETAILED DESCRIPTION OF THE PREFERRED EMBODIMENTS

First briefly in overview, the present invention presents both a novel technique for applying a staining agent for use in testing intraocular pressure via applanation tonometry, and a delivery system that enhances application thereof while minimizing pathogenic contamination. The technique is based on the selected introduction of a thin film of dried fluorescein on the forward end of the tonometer. The application of this thin film is accomplished concurrent with the disinfecting of the lens surface as the fluorescein is carried to the lens surface with a disinfecting solvent such as isopropyl alcohol. Importantly, the solvent is highly volatile and thus evaporates in a second or so, depending on the amount deposited. However, prior to evaporation, the contact time between the solvent and the smooth lens surface is sufficient to eradicate the pathogenic agents considered an infection risk during applanation tonometry.

The solvent containing the fluorescein is made of a disinfecting agent such as isopropyl or ethyl alcohol between 50 and 100 percent of the alcohol in an aqueous solution. The preferred concentration of alcohol is approximately 90 percent. The concentration of the fluorescein ranges between 0.01 and 1.0 percent of the total. The preferred concentration is 0.1 percent, but this may be adjusted to increase or decrease the final stain visibility during the applanation procedure. It may be that lower staining values are desired in instances where a contact lens may be used—a structure that might otherwise retain staining residue and discolor.

Figure 1:
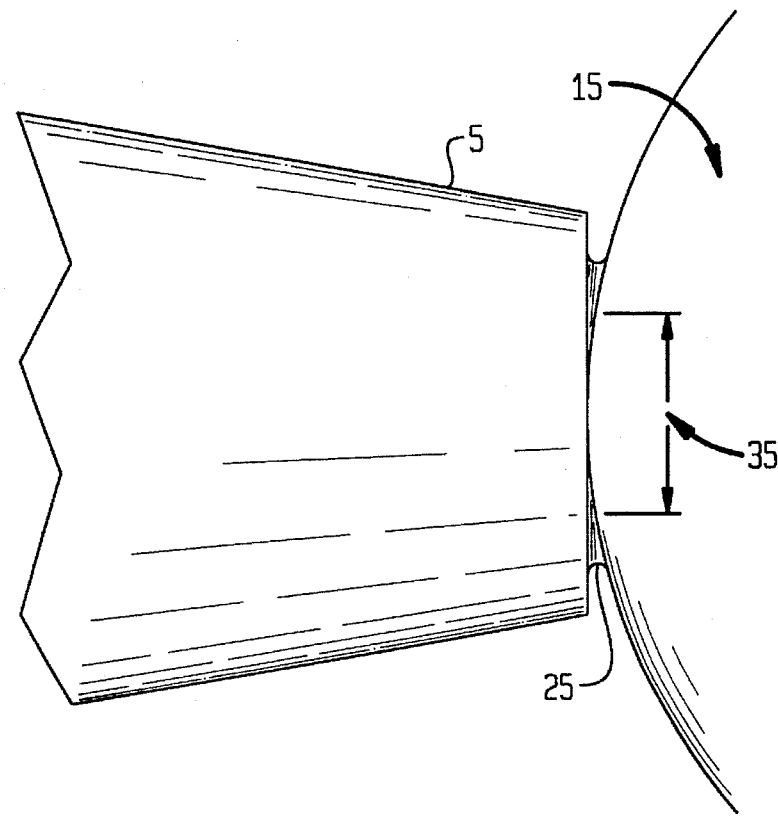
FIG. 1 depicts the tonometer lens in cross sectional side view in conjunction with the placement of the lens surface juxtaposed on the cornea tissue.
Figure 2:
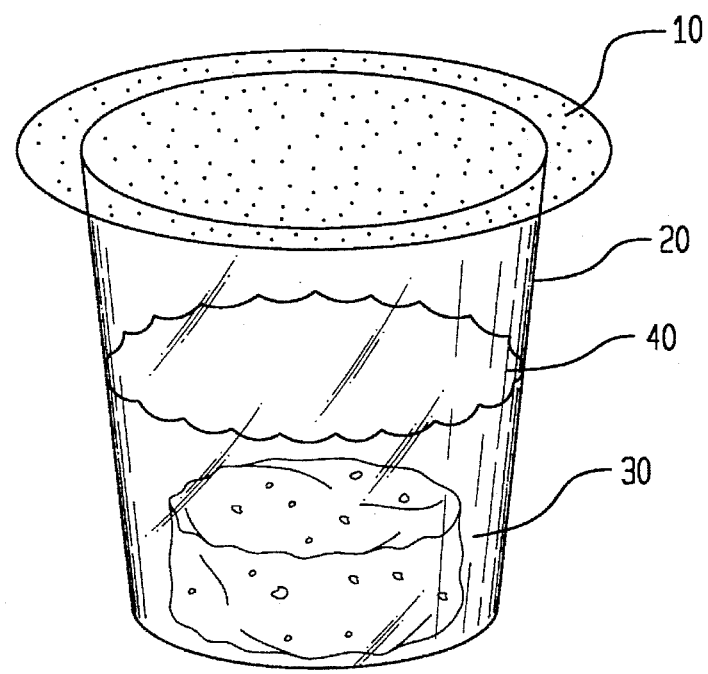
FIG. 2 depicts a preferred container for the fluorescein containing solvent in the context of the present invention.

Turning now to FIG. 2, a delivery system is depicted. In this arrangement the fluorescein containing solvent is held in a small multi-use cap container (20) having a thin film membrane (10) over its forward end to seal the insides thereof. The shape of the cap is selected to correspond to the front end of the tonometer, allowing the lens structure to partially insert itself into the cap when opened. The cap further contains a small absorbent pad (30) in its lower half as a retaining vehicle for the housed solvent (40).

The cap of FIG. 2 is used as follows. In preparation for the applanation procedure, the tonometer lens is taken to the open cap and inserted therein to the absorbent pad. The front of the lens is thus placed in contact with the pad which is otherwise saturated with the isopropyl alcohol solvent with 0.1 percent fluorescein. The lens in then withdrawn and within 1 to 2 seconds the isopropyl alcohol wetting on the lens surface evaporates leaving the thin film of fluorescein residue. The tonometer lens is then adjusted to the surface of the cornea—with contact therewith bringing the tear film of the eye into the fluorescein film and thus redissolving this film. Importantly, the dissolved fluorescein is now directly beneath the tonometer lens and therefor appears to the physician at the exact location required for accurate intraocular pressure measurement. Further, the minimal amount of fluorescein released inhibits an excessive or detrimental staining of the surrounding region or proximal contact lens. The measurements are made and the tonometer lens removed from the cornea; the cap is resealed and stored for later use.

The cap is made of a clear plastic to permit evaluation of the contents thereof. After numerous uses, the disinfecting solvent concentration will drop to a sub-useful level, via evaporation, indicated by a darkening of the cap solution—at this point the cap should be discarded.

Since other modifications and changes varied to fit particular operating requirements and environments will be apparent to those skilled in the art, the invention is not considered limited to the example chosen for the purposes of disclosure, and covers all changes and modifications which do not constitute departures from the true spirit and scope of this invention.

What is claimed is:

1. In combination in a method for examining the cornea of a patient's eye in a safe and non-intrusive way using applanation tonometry wherein a tonometer has a forward lens for contacting said cornea, comprising the steps of:

formulating a solution of fluorescein in a disinfectant solvent;

applying said solution to said lens of the tonometer;

allowing the solvent to evaporate leaving a thin film residue of fluorescein deposited on said lens surface;

contacting the lens with the cornea of the patient's eye thereby dissolving the thin film of fluorescein in the tear layer of the cornea and thus placing the fluorescein between the surface of the cornea and the tonometer lens;

wherein the fluorescein concentration of said fluorescein containing solution is selected to provide an amount between said lens and cornea upon application to effect staining of the cornea sufficiently to permit applanation tonometry to be completed.

2. The method of claim 1 wherein the fluorescein in solution has a concentration of between 0.01 to 1.0 percent.

3. The method of claim 2 wherein the fluorescein in solution is sodium fluorescein.

4. The method of claim 2 wherein the fluorescein in solution has a concentration of 0.1 percent.

5. The method of claim 1 wherein the solution is 50 to 100 percent isopropyl alcohol, 50 to 100 percent ethyl alcohol or a combination therof, any remainder of the solution comprising water.

6. The method of claim 5 therein the solution is approximately 90 percent isopropyl alcohol.

\* \* \* \* \*